United States Patent
Lee

(10) Patent No.: US 12,127,921 B2
(45) Date of Patent: Oct. 29, 2024

(54) SENSOR DEVICE FOR DIAPER

(71) Applicant: ATLab Inc., Yongin-si (KR)

(72) Inventor: Bang Won Lee, Yongin-si (KR)

(73) Assignee: ATLAB INC., Yongin-si (KR)

( * ) Notice: Subject to any disclaimer, the term of this patent is extended or adjusted under 35 U.S.C. 154(b) by 614 days.

(21) Appl. No.: 17/474,600

(22) Filed: Sep. 14, 2021

(65) Prior Publication Data

US 2021/0401636 A1    Dec. 30, 2021

Related U.S. Application Data

(63) Continuation-in-part of application No. PCT/KR2020/008443, filed on Jun. 29, 2020.

(30) Foreign Application Priority Data

Aug. 16, 2019 (KR) .................. 10-2019-0100053

(51) Int. Cl.
*A61F 13/42* (2006.01)
*A61B 5/00* (2006.01)
*G01N 27/22* (2006.01)

(52) U.S. Cl.
CPC .......... *A61F 13/42* (2013.01); *A61B 5/6808* (2013.01); *G01N 27/223* (2013.01); *G01N 27/227* (2013.01); *G01N 27/228* (2013.01); *A61F 2013/424* (2013.01)

(58) Field of Classification Search
CPC .... A61F 13/42; A61F 2013/424; A61F 13/44; A61B 5/6808; G01N 27/223; G01N 27/227; G01N 27/228
See application file for complete search history.

(56) References Cited

U.S. PATENT DOCUMENTS

| 7,221,279 B2 * | 5/2007 | Nielsen | A61F 13/42 340/384.1 |
| 9,230,999 B2 * | 1/2016 | Yu | H01L 27/1259 |
| 2004/0207530 A1 | 10/2004 | Nielsen | |
| 2012/0109087 A1 * | 5/2012 | Abraham | A61F 13/42 604/361 |
| 2014/0188063 A1 * | 7/2014 | Nhan | A61F 13/42 604/361 |

(Continued)

FOREIGN PATENT DOCUMENTS

| JP | 2000185067 | 7/2000 |
| KR | 20110107598 | 10/2011 |

(Continued)

OTHER PUBLICATIONS

International Search Report—PCT/KR2020/008443 dated Apr. 1, 2021.

*Primary Examiner* — Mohamed Barakat
(74) *Attorney, Agent, or Firm* — CANTOR COLBURN LLP

(57) ABSTRACT

A sensor device includes: a first protective layer; at least one pad positioned on an upper part of at least a part of the first protective layer; at least one sensing pattern layer positioned on an upper part of at least a part of the first protective layer and electrically connected to one of the at least one pad; a flexible body layer positioned on upper parts of the at least one pad and the at least one sensing pattern layer; and a shield plate layer positioned on an upper part of at least a part of the flexible body layer.

13 Claims, 4 Drawing Sheets

(56) References Cited

U.S. PATENT DOCUMENTS

2017/0265789 A1*  9/2017  Naseri ................ A61B 5/14507
2021/0077312 A1*  3/2021  Kim .................. A61F 13/15585
2021/0330516 A1* 10/2021  Letourneau .......... A61B 5/6826

FOREIGN PATENT DOCUMENTS

KR         101721084       3/2017
KR        20170099471      9/2017

* cited by examiner

SENSOR DEVICE FOR DIAPER

BACKGROUND OF THE INVENTION

Field of the Invention

The present disclosure relates to a sensor device for a diaper and, more particularly, to a sensor device for a diaper that is reusable and easily attached to an outer side of the diaper so that whether or not feces or/and urine are excreted may be detected.

Description of the Related Art

Recently, diaper wearing rates are increasing not only by infants but also by the elderly.

However, in a case where a diaper wearer has difficulty in communication, or is hesitant to communicate with other people due to his or her shame about discharging feces or/and urine, the diaper wearer is placed in an unsanitary state while wearing the unclean diaper for a long time.

In order to solve this problem, various sensor devices for diapers have been studied, but there is still a need for improving discomfort of the diaper wearer due to the sensor device, inconvenience of the sensor device attaching to and detaching from the diaper, and deterioration of durability of the sensor device due to the attachment and detachment thereof.

In addition, in order to cope with differences in positions of excreted feces or/and urine depending on gender, the sensor device for the diaper needs to detect the excreted feces or/and urine over a large area on the diaper.

SUMMARY OF THE INVENTION

An objective of the present disclosure is to solve the above-described technical problems, and the objective is to provide a sensor device for a diaper, wherein the sensor device may be mounted on an outer side of the diaper so as not to reduce comfort of wearing the diaper, be easily attachable to and detachable from the diaper, and improve a deterioration problem of durability of the sensor device due to the attachment and detachment thereof.

In addition, another objective of the present disclosure is to provide a sensor device for a diaper, the sensor device being able to cope with differences in positions of excreted feces or/and urine depending on gender by capability of detecting the excreted feces or/and urine over a large area of the diaper.

The sensor device for the diaper according to the present disclosure includes: a first protective layer; at least one pad positioned on an upper part of at least a part of the first protective layer; at least one sensing pattern layer positioned on an upper part of at least a part of the first protective layer and electrically connected to one of the at least one pad; a flexible body layer positioned on upper parts of the at least one pad and the at least one sensing pattern layer; and a shield plate layer positioned on an upper part of at least a part of the flexible body layer.

The sensor device for the diaper according to the present disclosure may detect whether feces or/and urine are excreted by using a change in capacitance value in the at least one pad or the at least one sensing pattern layer.

In addition, the sensor device for the diaper according to the present disclosure may preferably further include: a second protective layer positioned on upper parts of at least a part of the shield plate layer and at least a part of the flexible body layer; a printed circuit board layer positioned on an upper part of at least a part of the second protective layer or at least a part of the flexible body layer; a battery positioned on a same plane as the printed circuit board layer; a third protective layer configured to surround the printed circuit board layer and the battery; and a button layer positioned on an upper part of at least a part of the third protective layer and provided with at least one button.

In addition, the at least one sensing pattern layer may be formed by printing conductive ink or by using conductive fibers.

In addition, each of the at least one sensing pattern layer may include: a first connection pattern; a second connection pattern parallel to the first connection pattern; a plurality of third connection patterns connected to the first connection pattern, formed to be perpendicular to the first connection pattern, spaced apart from the second connection pattern, and arranged at equal intervals; and a plurality of fourth connection patterns connected to the second connection pattern, formed to be perpendicular to the second connection pattern, spaced apart from the first connection pattern, and arranged at equal intervals, wherein the third connection patterns and the fourth connection patterns are alternately arranged one by one.

Preferably, the at least one pad may be provided in a plural, and be sequentially arranged in a longitudinal direction of the sensor device for the diaper.

Specifically, the at least one pad may include: a first pad; a second pad; and a third pad, wherein the second pad and the third pad may be arranged at respective positions, facing each other, relative to the first pad as a center therebetween. In addition, the second pad may be connected to a first sensing pattern layer among the at least one sensing pattern layer, and the third pad may be connected to a second sensing pattern layer among the at least one sensing pattern layer.

In addition, the sensor device for the diaper according to the present disclosure may be configured to be attachable to the diaper by using at least one of a tape, a material having a sticky property in a form of a spray, and a material having the sticky property in a form of ink.

In addition, when measuring a change in capacitance value by using at least one of the at least one pad, a measuring power voltage may preferably be applied to a corresponding pad and a ground voltage is applied to the shield plate layer and remaining pads excluding the corresponding pad. When measuring the change in the capacitance value by using the shield plate layer, the ground voltage may characteristically be applied to all the pads and the power voltage is applied to the shield plate layer. That is, application of the power voltage to the at least one pad and the application of the power voltage to the shield plate layer may characteristically be performed at each different time.

According to a sensor device for a diaper of the present disclosure, since the sensor device is attachable to an outer side of the diaper, comfort of wearing the diaper may not be reduced, adverse effects on the skin may be prevented by way of not contacting the skin, the sensor device may be easily attached to and detached from the diaper, and a deterioration of durability due to the attachment and detachment thereof may be minimized.

In addition, according to the present disclosure, since feces or/and urine may be detected over a large area of the diaper, the present disclosure may cope with differences in positions of the excreted feces or/and urine in the diaper depending on gender.

DETAILED DESCRIPTION OF THE INVENTION

Hereinafter, a sensor device for a diaper according to an exemplary embodiment of the present disclosure is described in detail with reference to the accompanying drawings.

Naturally, it is apparent that the following examples of the present disclosure are not intended to limit or restrict the scope of the present disclosure, but only to embody the present disclosure. What can be easily inferred by those skilled in the art to which the present disclosure pertains from the detailed description and examples of the present disclosure is construed as belonging to the scope of the present disclosure.

Figure 1:
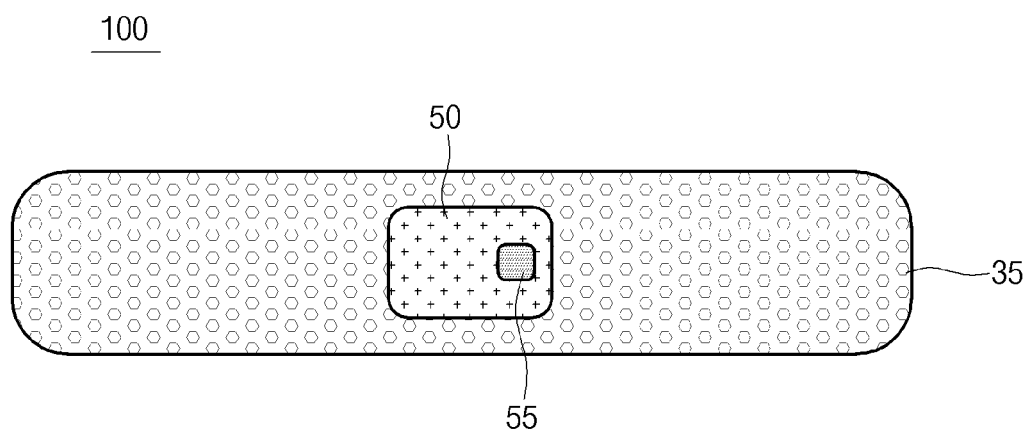
FIG. 1 is a plan view illustrating a sensor device for a diaper according to a preferred exemplary embodiment of the present disclosure.
Figure 2:
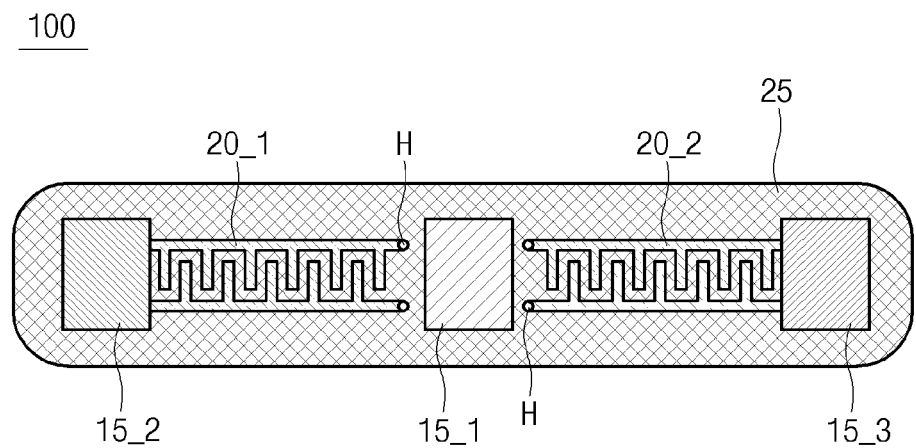
FIG. 2 is a bottom view illustrating the sensor device for the diaper according to the preferred exemplary embodiment of the present disclosure.
Figure 3:
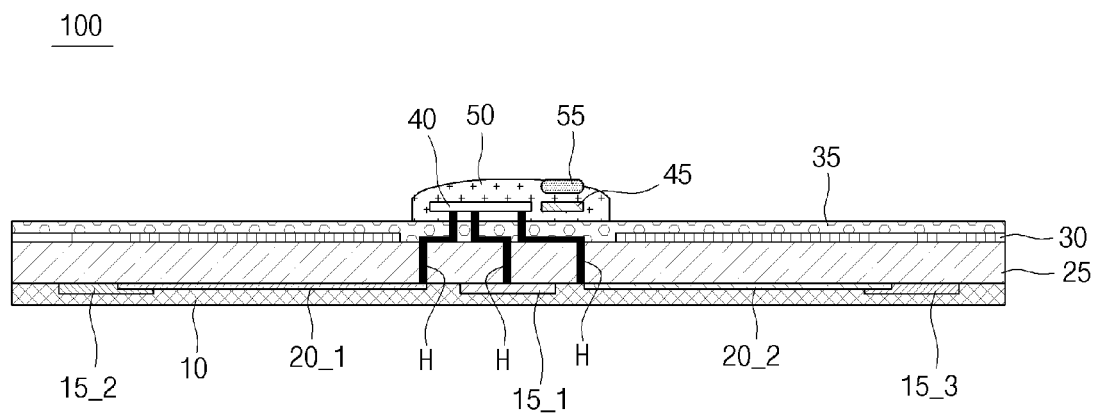
FIG. 3 is a sectional view illustrating the sensor device for the diaper according to the preferred exemplary embodiment of the present disclosure.

First, FIGS. 1 to 3 respectively illustrate a plan view, a bottom view, and a sectional view of a sensor device 100 for a diaper according to a preferred exemplary embodiment of the present disclosure. For reference, FIGS. 1 to 3 are illustrated by omitting some detailed configurations. In addition, FIG. 2 is the bottom view in a state where a first protective layer 10 is removed.

As may be seen from FIGS. 1 to 3, the sensor device for the diaper according to the preferred exemplary embodiment of the present disclosure is configured to include: the first protective layer 10; pads 15_1, 15_2, and 15_3; sensing pattern layers 20_1 and 20_2; a flexible body layer 25; a shield plate layer 30; a second protective layer 35; a printed circuit board layer 40; a battery 45; a third protective layer 50; and a button layer 55.

The first protective layer 10 and the second protective layer 35 serve to protect the pads 15_1, 15_2, and 15_3, the sensing pattern layers 20_1 and 20_2, the flexible body layer 25, and the shield plate layer 30. At least one of the pads 15_1, 15_2, and 15_3 is positioned on an upper part of at least a part of the first protective layer 10. The first protective layer 10 is preferably formed over the entire lower surface of the sensor device 100 for the diaper according to the present disclosure.

In addition, the at least one pad 15_1, 15_2, and 15_3 is preferably provided in plural, and is sequentially arranged in a longitudinal direction of the sensor device 100 for the diaper. By arranging each pad 15_1, 15_2, and 15_3 in the longitudinal direction of the sensor device 100 for the diaper, whether or not feces or/and urine are excreted on a large area of the diaper may be detected.

Specifically, the sensor device for the diaper according to the present disclosure may include, as the pads 15_1, 15_2, and 15_3, a first pad 15_1, a second pad 15_2, and a third pad 15_3. In addition, the second pad 15_2 and the third pad 15_3 are respectively arranged at positions, facing each other, relative to the first pad 15_1 as a center therebetween.

Each of the at least one sensing pattern layers 20_1 and 20_2 is positioned on an upper part of at least a part of the first protective layer 10, and is preferably electrically connected to one of the at least one pad 15_1, 15_2, and 15_3. That is, each one end of the sensing pattern layers 20_1 and 20_2 is positioned between the at least one pad 15_1, 15_2, and 15_3 and the flexible body layer 25, and is electrically connected to the at least one pad 15_1, 15_2, and 15_3 through physical contact.

Figure 4:
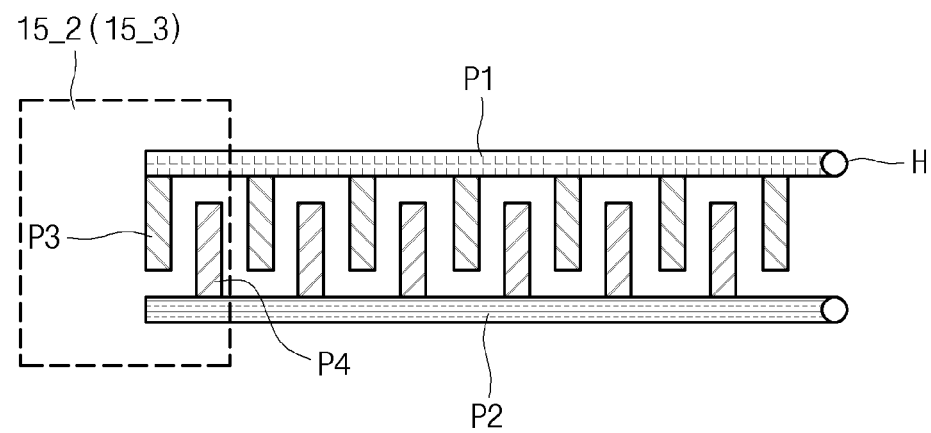
FIG. 4 is a plan view illustrating a sensing pattern layer connected to each of pads.

The at least one sensing pattern layer 20_1 and 20_2 is formed of a conductive material, and may be formed by printing conductive ink, or be formed by using conductive fibers. That is, the at least one sensing pattern layer 20_1 and 20_2 is preferably formed of a material having a thickness thinner than that of each pad 15_1, 15_2, and 15_3. FIG. 4 is a plan view illustrating pads 15_1, 15_2, and 15_3, and sensing pattern layers 20_1 and 20_2 respectively connected to the pads 15_1, 15_2, and 15_3.

As may be seen from FIG. 4, each of the at least one sensing pattern layer 20_1 and 20_2 preferably has a shape of a finger alternately arranged with each other.

That is, each of the at least one sensing pattern layer 20_1 and 20_2 is configured to include; a first connection pattern P1; a second connection pattern P2 parallel to the first connection pattern P1; a plurality of third connection patterns P3 connected to the first connection pattern P1, formed to be perpendicular to the first connection pattern P1, spaced apart from the second connection pattern P2, and arranged at equal intervals; and a plurality of fourth connection patterns P4 connected to the second connection pattern P2, formed to be perpendicular to the second connection pattern P2, spaced apart from the first connection pattern P1, and arranged at equal intervals.

In addition, characteristically, each third connection pattern P3 and each fourth connection pattern P4 are alternately arranged one by one, respectively.

By the at least one sensing pattern layer 20_1 and 20_2, the sensor device 100 for the diaper of the present disclosure may detect whether or not feces or/and urine are excreted not only in an area of the pads 15_1, 15_2, and 15_3, but also in an area of the sensing pattern layers 20_1 and 20_2. In addition, as each width of the third connection pattern P3 and fourth connection pattern P4 of the sensing pattern layers 20_1 and 20_2 is narrow and each distance between the patterns is denser, whether or not the feces or/and urine are excreted may be detected with a higher sensitivity.

That is, despite the limited number of pads 15_1, 15_2, and 15_3, the sensor device 100 for the diaper of the present disclosure may detect whether or not feces or/and urine are excreted in a large area of the diaper by using the sensing pattern layers 20_1 and 20_2.

Specifically, the second pad 15_2 is connected to the first sensing pattern layer 20_1 among the at least one sensing pattern layer 20_1 and 20_2. In addition, the third pad 15_3 is connected to the second sensing pattern layer 20_2 among the at least one sensing pattern layer 20_1 and 20_2. In addition, it is preferable that the first sensing pattern layer 20_1 and the second sensing pattern layer 20_2 are symmetrical relative to the first pad 15_1.

The sensor device 100 for the diaper according to the present disclosure is characterized by detecting whether or not feces or/and urine are excreted by using a change in capacitance value in the pads 15_1, 15_2, and 15_3 or the sensing pattern layers 20_1 and 20_2.

The capacitance value may be measured for each group composed of: a first pad group including the first pad 15_1; a second pad group including the second pad 15_2 and the first sensing pattern layer 20_1; and a third pad group including the third pad 15_3 and the second sensing pattern layer 20_2. In addition, the capacitance value may be measured between one group and another group. In this case, it is necessary to connect the power source and ground for each group differently. Since the measurement of capacitance value in a capacitive sensor is common, a detailed description thereof will be omitted. In addition, in the present disclosure, although only one example of the pads 15_1, 15_2, and 15_3 and the sensing pattern layers 20_1 and 20_2 has been described, it is apparent that there may be various sensing pads and sensing pattern layers.

The flexible body layer 25 is positioned on upper parts of the at least one pad 15_1, 15_2, and 15_3 and the at least one sensing pattern layer 20_1 and 20_2. Specifically, the flexible body layer 25 may be implemented by using silicone rubber or a flexible substrate.

Holes H need to be formed in the flexible body layer 25 and the second protective layer 35, which are connected to at least one end of the at least one sensing pattern layer 20_1 and 20_2. The at least one sensing pattern layer 20_1 and 20_2 is electrically connected to the printed circuit board layer 40 by plating each hole H or connecting wiring thereto through each hole H.

In addition, the holes H are formed in the flexible body layer 25 and the second protective layer 35, which are connected to the first pad 15_1 that is not connected to the sensing pattern layers 20_1 and 20_2, so that the first pad 15_1 and the printed circuit board layer 40 are electrically connected to each other.

The shield plate layer 30 is positioned on an upper part of at least a part of the flexible body layer 25.

By blocking recognition of an external touch by a person with respect to the sensor device 100 for the diaper of the present disclosure, the shield plate layer 30 prevents erroneous operation of detecting the external touch by the person as a case in which feces or/and urine are excreted. That is, in the case where at least one of the pads 15_1, 15_2, and 15_3 detects whether the feces or/and urine are excreted, the shield plate layer 30 may remove an obstructive factor caused by a person.

However, by varying voltage connection from the printed circuit board layer 40 to the at least one pad 15_1, 15_2, and 15_3 and the shield plate layer 30, the shield plate layer 30 may also be used to detect a human touch, that is, whether fingers come in proximity.

Figure 5:
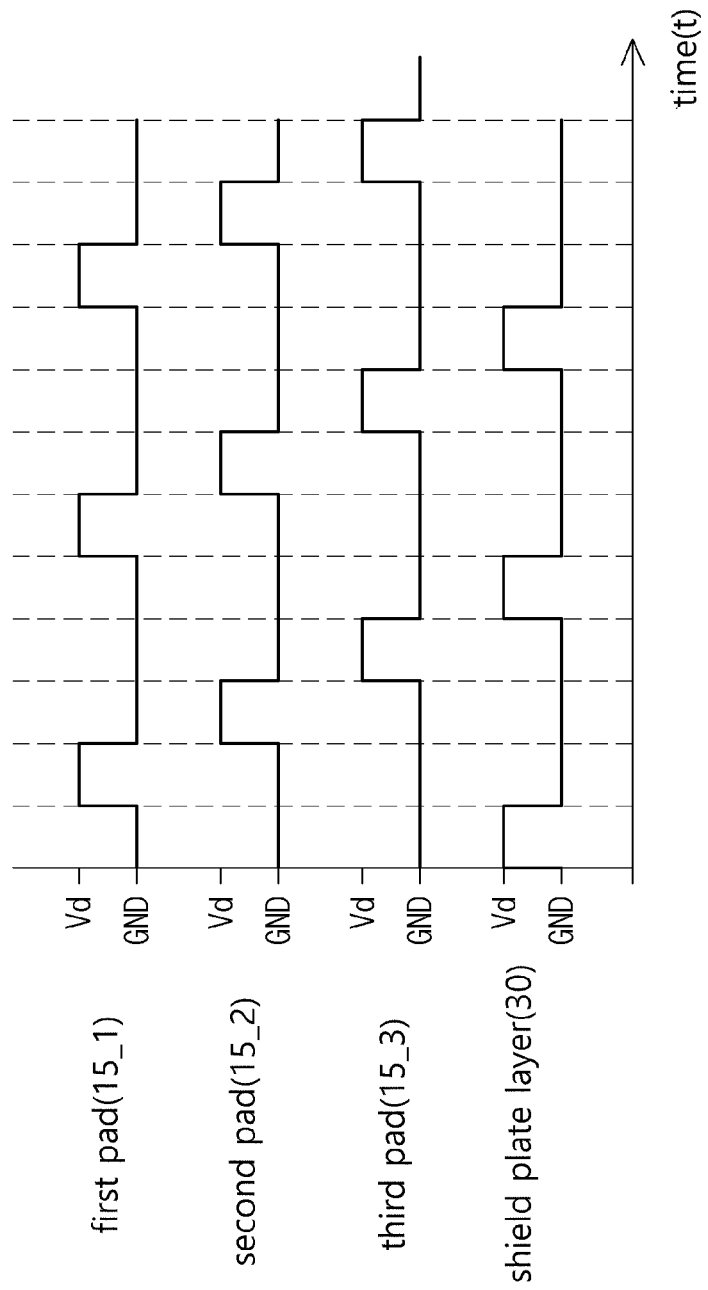
FIG. 5 is a view illustrating an example of voltage application to at least one pad and a shield plate layer.

FIG. 5 is a view illustrating an example of voltage application to at least one of the pads 15_1, 15_2, and 15_3 and the shield plate layer 30.

As may be seen from FIG. 5, when a change in capacitance value is measured by using at least one of the at least one pad 15_1, 15_2, and 15_3, the measuring power voltage is applied to a corresponding pad, and the ground voltage is applied to the remaining pads and the shield plate layer 30. In addition, when measuring the change in the capacitance value by using the shield plate layer 30, it is preferable that the ground voltage is applied to all the pads 15_1, 15_2, and 15_3, and the power voltage is applied to the shield plate layer 30.

That is, it is characterized in that application of a measuring power voltage to the at least one pad 15_1, 15_2, and 15_3 and the application of the power voltage to the shield plate layer 30 are performed at each different time.

Specifically, it is preferable that the application of the power voltage to the first pad 15_1, the second pad 15_2, the third pad 15_3, and the shield plate layer 30 is performed by a time-sharing method. That is, when the power voltage is applied to one of components including the first pad 15_1, the second pad 15_2, the third pad 15_3, and the shield plate layer 30, the ground voltage is applied to the remaining components excluding the component to which the power voltage is applied. Among the first pad 15_1, the second pad 15_2, the third pad 15_3, and the shield plate layer 30, the component to which the power voltage is applied is operated so as to perform the measurement. In addition, when the at least one pad 15_1, 15_2, and 15_3 is operated, whether feces or/and urine are excreted is detected, and when the shield plate layer 30 is operated, whether fingers come in proximity is detected.

The second protective layer 35 is positioned on upper parts of at least a part of the shield plate layer 30 and at least a part of the flexible body layer 25. In addition, the second protective layer 35 preferably covers the shield plate layer 30 and the entire upper surface of the flexible body layer 25 on which the shield plate layer 30 is not covered.

The printed circuit board layer 40 is positioned on an upper part of at least a part of the second protective layer 35 or at least a part of the flexible body layer 25. The printed circuit board layer 40 may be mounted on an upper part of the flexible body layer 25 without the second protective layer 35. That is, it is preferable to use a flexible FPCB in which electronic components are mounted. In addition, the printed circuit board layer 40 is electrically connected to the first pad 15_1, the first sensing pattern layer 20_1, the second sensing pattern layer 20_2, and the shield plate layer 30, respectively, so that the capacitance value can be measured.

In addition, although the present disclosure has been described the electronic component for measuring only the capacitance value, it is apparent that various functions such as measurement of bio-signals, physical characteristics (i.e., movement, tilt, etc.), voice signals, and the like may be provided. In addition, it is apparent that the signals may be digitized and stored in a memory or transmitted wirelessly to the outside.

The battery 45 is preferably positioned on the same plane as the printed circuit board layer 40. By arranging the printed circuit board layer 40 and the battery 45 side by side, the thickness of the sensor device 100 for the diaper according to the present disclosure may be formed thin. The battery 45 serves to supply power to the printed circuit board layer 40.

The third protective layer 50 serves to surround and protect the printed circuit board layer 40 and the battery 45. It is preferable that the third protective layer 50 covers not only the upper parts of the printed circuit board layer 40 and the battery 45, but also the side surfaces thereof. In addition, in some cases, the third protective layer 50 may also cover the lower parts of the printed circuit board layer 40 and the battery 45.

In addition, although it has been described that the first pad 15_1 and the third protective layer 50 are arranged at a position in a middle region of the sensor device in FIGS. 2 and 3, the position may be changed to any position thereof.

The button layer 55 is positioned on an upper part of at least a part of the third protective layer 50, and includes at least one button. That is, the upper part of the button layer 55 is preferably exposed to the outside for use of a user. By using at least one button provided in the button layer 55, the user may perform at least one of operations including: supplying or blocking power from the battery 45 to the printed circuit board layer 40; resetting the printed circuit board layer 40; and operating a specific function by using the time interval and number of times in which the button is pressed.

Although the present disclosure has been described with the third protective layer 50, it is apparent that an embodiment may be implemented by applying with an outward form in a rigid type. In addition, although the present disclosure has been briefly described with the button layer 55, it is apparent that a plurality of input signals may be generated in the form of touching.

The sensor device 100 for the diaper of the present disclosure may cover all of the components exhibiting internal conductivity by the first protective layer 10, the second protective layer 35, and the third protective layer 50, thereby having strong durability.

For reference, the sensor device 100 for the diaper of the present disclosure is preferably manufactured in a thin rectangular shape having a thickness of about 4 mm and a length of about 150 mm.

The sensor device 100 for the diaper according to the present disclosure may be configured to be attachable to the diaper by using a tape. For reference, the tape includes a double-sided tape or hook and loop fasteners.

Figure 6:
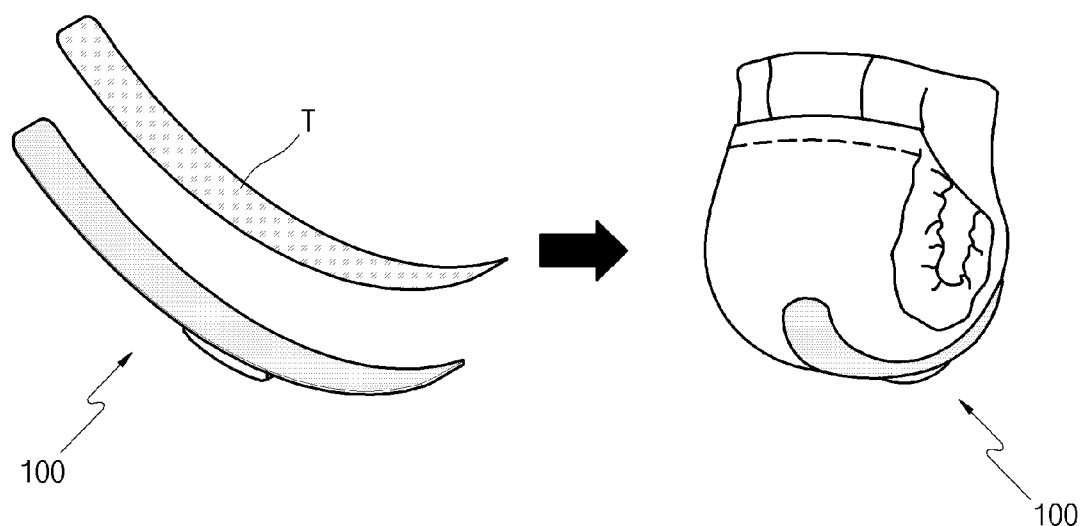
FIG. 6 is a view illustrating an example of attaching, to the diaper, the sensor device for the diaper of the present disclosure.

FIG. 6 is a view illustrating an example of attaching, to a diaper, the sensor device for the diaper of the present disclosure.

In the sensor device 100 for the diaper of the present disclosure, the sensor device made of a flexible material is bendable, and is usable by way of attaching one side of a double-sided tape T to the first protective layer 10 and attaching the other side of the double-sided tape T to the diaper. However, in addition to the double-sided tape T, a material having a sticky property in the form of a spray, a material having a sticky property in the form of ink, or hook and loop fasteners may also be used for attaching, to a diaper, the sensor device 100 for the diaper of the present disclosure. For reference, a material having a sticky property refers to a material having an adhesive property.

The diaper has an absorbent layer inside a waterproof layer, and a change in the absorbent layer when feces or/and urine are excreted by a wearer is measured as a change in capacitance value by the sensor device 100 for the diaper of the present disclosure.

The sensor device 100 for the diaper according to the present disclosure is attached to the outer side of the diaper to improve the wearer's discomfort. In addition, by using at least one of the following including: the double-sided tape T; hook and loop fasteners; the material having the sticky property in the form of the spray; or the material having the sticky property in the form of ink, the ease of attachment and detachment thereof to the diaper may be improved and the deterioration problem of durability due to the attachment and detachment thereof may also be improved.

In addition, the sensor device 100 for the diaper of the present disclosure may detect feces or/and urine excreted over the large area of the diaper by the plurality of pads 15_1, 15_2, and 15_3 and the sensing pattern layers 20_1 and 20_2, so whether the feces or/and urine are excreted may be detected with high sensitivity despite the differences in the positions of the excreted feces or/and urine depending on gender. In addition, in the sensor device 100 for the diaper of the present disclosure, the plurality of pads 15_1, 15_2, and 15_3 and the sensing pattern layers 20_1 and 20_2 operate as capacitive sensors, and use the measured capacitance value to measure the amount of feces or/and urine as well.

In addition, the sensor device 100 for the diaper of the present disclosure may also detect whether fingers come in proximity to the sensor device 100 for the diaper by using the shield plate layer 30.

What is claimed is:

1. A sensor device for a diaper, the sensor device comprising:
    a first protective layer;
    at least one pad positioned on an upper part of at least a part of the first protective layer;
    at least one sensing pattern layer positioned on an upper part of at least a part of the first protective layer and electrically connected to one of the at least one pad; and
    a flexible body layer positioned on upper parts of the at least one pad and the at least one sensing pattern layer;
    wherein each of the at least one sensing pattern layer comprises:
    a first connection pattern;
    a second connection pattern parallel to the first connection pattern;
    a plurality of third connection patterns connected to the first connection pattern, formed to be perpendicular to the first connection pattern, spaced apart from the second connection pattern, and arranged at equal intervals; and
    a plurality of fourth connection patterns connected to the second connection pattern, formed to be perpendicular to the second connection pattern, spaced apart from the first connection pattern, and arranged at equal intervals,
    wherein the third connection patterns and the fourth connection patterns are alternately arranged one by one.

2. The sensor device of claim 1, further comprising:
    a shield plate layer positioned on an upper part of at least a part of the flexible body layer.

3. The sensor device of claim 1, wherein the sensor device for the diaper detects whether feces or/and urine are excreted by using a change in capacitance value in the at least one pad or the at least one sensing pattern layer.

4. The sensor device of claim 2, further comprising:
    a second protective layer positioned on upper parts of at least a part of the shield plate layer and at least a part of the flexible body layer; and
    a printed circuit board layer positioned on an upper part of at least a part of the second protective layer or at least a part of the flexible body layer.

5. The sensor device of claim 4, further comprising:
    a battery positioned on a same plane as the printed circuit board layer.

6. The sensor device of claim 5, further comprising:
    a third protective layer configured to surround the printed circuit board layer and the battery.

7. The sensor device of claim 1, wherein the at least one sensing pattern layer is able to be formed by printing conductive ink or by using conductive fibers.

8. The sensor device of claim 1, wherein the at least one pad is provided in a plural, and is sequentially arranged in a longitudinal direction of the sensor device for the diaper.

9. The sensor device of claim 8, wherein the at least one pad comprises:
    a first pad;
    a second pad; and
    a third pad, wherein the second pad and the third pad are arranged at respective positions, facing each other, relative to the first pad as a center therebetween.

10. The sensor device of claim 9, wherein the second pad is connected to a first sensing pattern layer among the at least one sensing pattern layer, and the third pad is connected to a second sensing pattern layer among the at least one sensing pattern layer.

11. The sensor device of claim 1, wherein the sensor device for the diaper is configured to be attachable to the diaper by using at least one of a tape, a material having a sticky property in a form of a spray, and a material having the sticky property in a form of ink.

12. The sensor device of claim 2, wherein, when measuring a change in capacitance value by using at least one of the at least one pad, a measuring power voltage is applied to a corresponding pad and a ground voltage is applied to the shield plate layer and remaining pads excluding the corresponding pad, and when measuring the change in the capacitance value by using the shield plate layer, the ground voltage is applied to all the pads and the power voltage is applied to the shield plate layer.

13. The sensor device of claim 2, wherein application of a measuring power voltage to the at least one pad and the application of the power voltage to the shield plate layer are performed at each different time.

\* \* \* \* \*